US012534703B2

(12) United States Patent
Kim et al.

(10) Patent No.: US 12,534,703 B2
(45) Date of Patent: Jan. 27, 2026

(54) CELL CULTURE SUBSTRATE AND MANUFACTURING METHOD THEREFOR

(71) Applicant: AMOLIFESCIENCE CO., LTD., Seoul (KR)

(72) Inventors: Hyeong Taek Kim, Seoul (KR); Dong Sik Seo, Seoul (KR); Hui Gwan Goo, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 847 days.

(21) Appl. No.: 17/788,886

(22) PCT Filed: Dec. 28, 2020

(86) PCT No.: PCT/KR2020/019215

§ 371 (c)(1),
(2) Date: Jun. 24, 2022

(87) PCT Pub. No.: WO2021/133143

PCT Pub. Date: Jul. 1, 2021

(65) Prior Publication Data

US 2023/0056844 A1 Feb. 23, 2023

(30) Foreign Application Priority Data

Dec. 27, 2019 (KR) ........................ 10-2019-0177073

(51) Int. Cl.
*C12N 5/00* (2006.01)

(52) U.S. Cl.
CPC ........ *C12N 5/0068* (2013.01); *C12N 2533/50* (2013.01)

(58) Field of Classification Search
None
See application file for complete search history.

(56) References Cited

U.S. PATENT DOCUMENTS 10,017,548 B2 7/2018 Malley et al.
11,248,201 B2 2/2022 Jang et al.
2005/0058842 A1 3/2005 Liebmann-Vinson et al.
2015/0010999 A1* 1/2015 Caracci ................ C12N 5/0606 435/396
2015/0252148 A1* 9/2015 Lee ......................... A61L 27/56 435/395
2016/0355780 A1 12/2016 Kim et al.
2019/0203178 A1 7/2019 Seo et al.
2020/0318049 A1 10/2020 Koo et al.

FOREIGN PATENT DOCUMENTS

| | | | | |
|---|---|---|---|---|
| CN | 109196092 | A | 1/2019 | |
| CN | 109568649 | A | 4/2019 | |
| JP | 2017147951 | A | 8/2017 | |
| KR | 101311325 | A | 9/2013 | |
| KR | 20140053903 | A | 5/2014 | |
| KR | 20160036681 | A | 4/2016 | |
| KR | 20170132994 | A | 12/2017 | |
| KR | 20170135769 | A | 12/2017 | |
| WO | WO-2017209521 | A1 * | 12/2017 | ............. A61L 27/14 |
| WO | 2019013580 | A | 1/2019 | |

OTHER PUBLICATIONS

International Search Report cited in PCT/KR2020/019215 dated Apr. 8, 2021, 9 pages.

* cited by examiner

*Primary Examiner* — Tracy Vivlemore
*Assistant Examiner* — Catherine L McCormick
(74) *Attorney, Agent, or Firm* — ROTHWELL, FIGG, ERNST & MANBECK, P.C.

(57) ABSTRACT

A cell culture substrate including a fibrous web in which fibers are integrated, and a cell culture coating layer comprising a coating film connecting at least some fibers from among fibers positioned on one surface of the fibrous web, wherein the cell culture coating layer is realized through a fusion protein for cell culture in which a functional peptide is bound to a mussel adhesive protein. Thus, the substrate can be stored at room temperature for a long period of time, i.e., several years, despite containing protein-like substances that aid in cell culture, and thus exhibits very high storage stability. At the same time, the activity of substances that aid in cell culture is maintained at the same level or is reduced only minimally, thus enabling cell culture at an initially designed level.

11 Claims, 12 Drawing Sheets

Specification includes a Sequence Listing.

CELL CULTURE SUBSTRATE AND MANUFACTURING METHOD THEREFOR

CROSS REFERENCE TO RELATED APPLICATIONS

This application is a 35 U.S.C. 371 National Phase Entry application from PCT/KR2020/019215 filed Dec. 28, 2020, which claims priority to and the benefit of Korean Patent Application No. 10-2019-0177073, filed on Dec. 27, 2019, the disclosures of which are incorporated herein by reference in their entirety.

The present application includes a Sequence Listing filed in electronic format. The Sequence Listing is entitled SOP115925US_ST25 created on Jun. 23, 2022 and is 13,000 bytes in size. The information in the electronic format of the Sequence Listing is part of the present application and is incorporated herein by reference in its entirety.

TECHNICAL FIELD

The present invention relates to a cell culture substrate and manufacturing method thereof.

BACKGROUND

Recently, as the use of cultured cells for disease treatment is expanded, interest and research on cell culture are increasing. Cell culture is a technology for collecting cells from a living body and culturing them outside the living body. The cultured cells can be differentiated into various tissues of the body, such as skin, organs, and nerves, and then transplanted into the human body or the culture cells can be transplanted into the human body in a state before differentiation to achieve engraftment and differentiation at the same time, so that they can be used for treating various diseases.

Cultivation of mammalian cells is one of many processes in the life sciences and health sciences. As a cell culture substrate for mammalian cell culture and analysis including anchorage-dependent cells, a vessel such as a well-plate made of, for example, a high molecular polymer or glass, or a plate such as a film, is often used. Here, additional surface treatment is required to allow the cells to adhere to the surface of the vessel or plate. Such surface treatment may include, for example, forming an adsorption layer on the surface or implementing an appropriate surface shape by adsorption, grafting, or plasma polymerization techniques. Alternatively, the surface treatment may be achieved through chemical modification of the surface itself of the container or plate, for example, atmospheric corona, radio frequency vacuum plasma, DC glow discharge, and microwave plasma treatment.

On the other hand, current methods for culturing, differentiating, cross-differentiating, and reprogramming various stem cells including, for example, adult stem cells (ASCs) and pluripotent stem cells and somatic cells, generally require complex culture environments, for example, a microenvironment similar to an extracellular matrix, to culture the stem cells. The microenvironment is formed by forming a coating layer using extracellular matrix proteins or other various proteins helpful for cell proliferation on the surface of a solid substrate.

On the other hand, the coating layer is formed by simply treating a solution containing the above-described various proteins on a cell adhesion surface such as a container or plate and then drying. However, the stability of the protein activity in the coating layer is very low, and there is a problem in that the activity is easily lost within a few hours at room temperature after the coating layer is formed. Therefore, it is difficult to manufacture a cell culture substrate having the coating layer formed in advance, and even if it is manufactured, the cell culture substrate must be stored at a low temperature, and even when stored at a low temperature, the storage days are very short, within 30 days. In addition, due to such poor storage stability, it is common to form the coating layer on the cell adhesion surface immediately before cell loading operation, which causes inconvenience in cell culture operation and prolongs the preparation time before cell culture.

SUMMARY OF THE INVENTION

The present invention has been devised in consideration of the above, and an object of the present invention is to provide a cell culture substrate which can be stored at room temperature for a long period of time over several years, exhibiting excellent storage stability, while activities of compounds that are beneficial to culturing of the cells remain unchanged or only suffer minimal degradation so that the cells can be cultured at an initially-designed level, and a method for manufacturing the same.

Further, another object of the present invention is to provide a cell culture substrate which can have an excellent cell adhesion capability and allow reliable proliferation of the cells attached thereto, and thus can achieve a high cell culture efficiency, and a method for manufacturing the same.

Furthermore, another object of the present invention is to provide a cell culture coating composition that can achieve the above excellent properties.

In order to achieve the above object, the present invention provides a cell culture substrate, including a fibrous web in which fibers are integrated, and a cell culture coating layer comprising a coating film connecting at least some of the fibers positioned on one surface of the fibrous web, wherein the cell culture coating layer is formed with a fusion protein for cell culture in which a functional peptide is bound to a mussel adhesive protein.

According to one embodiment of the present invention, the functional peptide may have a function of promoting any one or more of adhesion, migration, proliferation and differentiation of a cell.

In addition, the fibrous web may include any one or more components selected from the group consisting of polystyrene (PS), polyester, polyethersulfone (PES), polyvinylidene fluoride (PVDF), polydimethylsiloxane (PDMS), polyamide, polyimide, polyethylene and polypropylene.

In addition, the mussel adhesive protein may be any one protein selected from the group consisting of amino acid sequences of SEQ ID NO: 1 to SEQ ID NO: 14, or a protein to which one or more amino acid sequences selected from the group are linked.

The functional peptide may include an RGD sequence.

The functional peptide may be any one or more peptides selected from the group consisting of amino acid sequences of SEQ ID NO: 15 to SEQ ID NO:19, or a peptide to which one or more amino acid sequences selected from the group are linked.

In addition, the cell culture substrate may further include a support disposed on the other surface opposite to the one surface of the fibrous web.

The fibrous web may have an average diameter of 200 to 1000 nm, a thickness of 2 to 20 μm, and a basis weight of 3 to 20 g/$m^2$.

In addition, the present invention provides a method for manufacturing a cell culture substrate, including the steps of (1) preparing an active solution containing a carbodiimide-based coupling agent and a reactive agent and a fusion protein for cell culture in which a functional peptide is bound to a mussel adhesive protein, (2) preparing a cell culture coating composition by mixing the prepared active solution and the prepared fusion protein for cell culture, and (3) forming a cell culture coating layer by treating the cell culture coating composition on a surface of a fibrous web.

According to one embodiment of the present invention, the carbodiimide-based coupling agent may be 1-ethyl-3-(3-dimethylaminopropyl carbodiimide hydrochloride (EDC) or N,N'-dicyclohexylcarboimide (DCC), and the reactive agent may be N-hydroxysuccinimide (NHS) or N-hydroxysulfosuccinimide (Sulfo-NHS).

In addition, the carbodiimide-based coupling agent and the reactive agent may be contained in the active solution in a weight ratio of 1:0.1 to 10. In the cell culture coating composition, the carbodiimide-based coupling agent may be mixed in an amount of 1:1 to 100 parts by weight with respect to 100 parts by weight of the fusion protein for cell culture.

In addition, the present invention provides a cell culture coating composition for a porous cell culture substrate which forms a coating layer that blocks at least some pores on a surface of the porous cell culture substrate, the cell culture coating composition including a fusion protein for cell culture in which a functional peptide is bound to a mussel adhesive protein, a carbodiimide-based coupling agent, and a reactive agent.

Hereinafter, the terms used in the present invention will be described.

The term "extracellular matrix (ECM)" used in the present invention is a matrix that surrounds the outside of a cell, occupies between cells, and means having a network structure mainly composed of proteins and polysaccharides.

Despite containing compounds such as proteins that are beneficial to culturing cells, the cell culture substrate according to the present invention can be stored at room temperature for a long period of time over several years, exhibiting excellent storage stability, while activities of such compounds that are beneficial to culturing of the cells remain unchanged or only suffer minimal degradation so that the cells can be cultured at an initially-designed level. Further, since the cell adhesion capability to the cell culture substrate is excellent and the cells attached thereto can be reliably proliferated, a high cell culture efficiency can be achieved. Accordingly, the cell culture substrate can be widely utilized for culturing various cells including stem cells.

DETAILED DESCRIPTION

Figure 1:
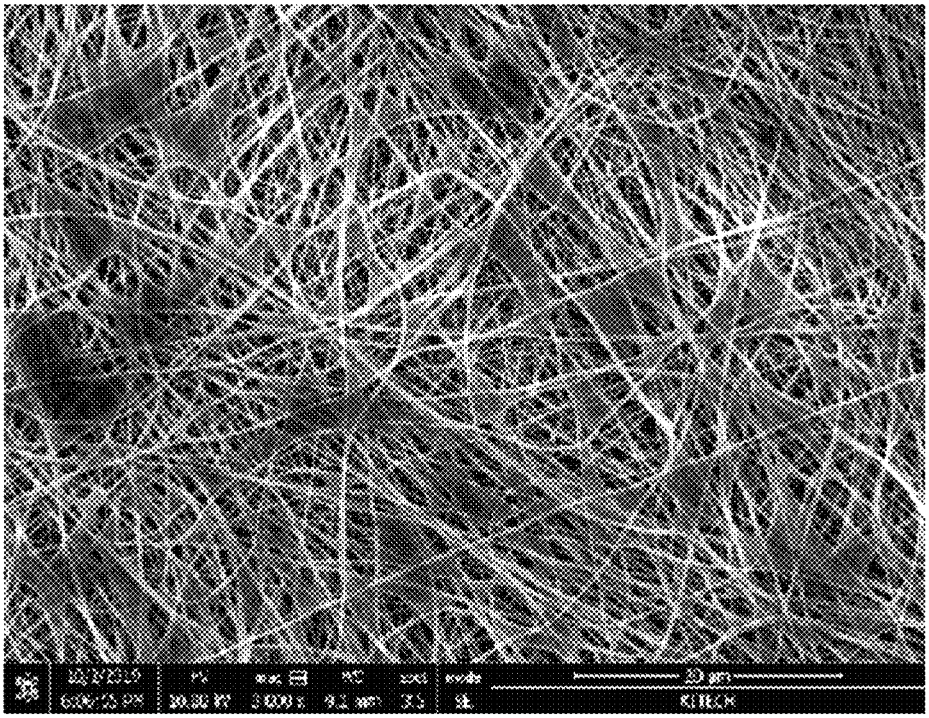
FIGS. 1 and 2 respectively show a SEM photograph of a surfaces of a cell culture substrate according to an example of the present invention.

Hereinafter, with reference to the accompanying drawings, the embodiments of the present invention will be described in detail so that those of ordinary skill in the art to which the present invention pertains can easily implement them. The present invention may be embodied in many different forms and is not limited to the embodiments described herein.

The cell culture substrate according to an embodiment of the present invention includes a fibrous web in which fibers are integrated and a cell culture coating layer.

The fibrous web provides a surface to be coated for the cell culture coating layer to be described later as a support on which seeded cells can settle and proliferate. The fibrous web has a three-dimensional network structure in which fibers are integrated, and specifically, each fiber is independently folded and/or arranged without determining the fiber length direction, and by stacking them, it is possible to form a structurally more complex and various three-dimensional network structure. The complex and variously formed internal structure functions as a flow path for a culture solution containing nutrients necessary for cell proliferation, and can easily supply nutrients to the cells positioned inside the fibrous web, prevent apoptosis, and promote cell proliferation.

In this case, adhesion or fusion may occur between different surfaces within a single-stranded fiber and/or between the surfaces of different fibers, and through this, the three-dimensional network structure may be more structurally stabilized.

In addition, the surface of the fibrous web formed by randomly arranging and accumulating fibers can induce a three-dimensional culture of cells by the surface morphology. As an example of the surface morphology, the surface of the fibrous web may not be flat, and an uneven surface may be formed on the surface, and the surface roughness may be large. The roughness of the surface shape of the fibrous web includes, for example, a plurality of concave and/or convex portions. Thus, in addition to the effect of the three-dimensional growth of cells, the cells can be more easily and firmly seated in the space between the convex portions or the grooves of the concave portions. Accordingly, it has an advantage of significantly reducing the number of cells detached after being seated on the cell culture sheet.

For the fibers forming the fibrous web, materials commonly used in cell culture may be used without limitation. As an example, the fiber may include any one or more components selected from the group consisting of polyester such as polystyrene (PS), polyethylene terephthalate and polycarbonate, fluorine-based compounds such as polyethersulfone (PES), polyvinylidene fluoride (PVDF), polydimethylsiloxane (PDMS), polyamide, polyimide, polyethylene, and polypropylene. However, in consideration of both cell proliferation and recovery, the fiber may include a fluorine-based compound, of which polyvinylidene fluoride (PVDF) may be included. When the fiber is PVDF, it may be advantageous to not only have excellent cell recovery properties, but also to realize that the diameter of the cultured cell is smaller than the cell diameter at the time of seeding.

The fibrous web may be embodied in a web shape by a known method such as spunbonding or melt blown, or may be embodied through electrospinning. In addition, the fibrous web is formed of fibers having an average diameter of 10 nm to 1.5 μm, and may have a basis weight of 1 to 20 $g/m^2$. If the average diameter of the fibers is less than 10 nm, the mechanical strength is inferior, and it may be difficult to manufacture the fibrous web. If the average diameter of the fibers exceeds 1.5 μm, the density (basis weight) of the fibrous web is reduced, and there is a risk that the surface of the fibrous web is partially melted during thermocompression bonding. In addition, since it is difficult for the fibrous web morphology to realize a topology advantageous for cell culture, there is a risk that cell culture efficiency may decrease. In addition, if the basis weight is less than 1 $g/m^2$, there is a risk that handling is not easy when manufacturing the fibrous web. If the basis weight exceeds 20 $g/m^2$, the fibrous web may be melted in the pressing roll, and it may be difficult to adhere to a separate support film when the fibrous web is laminated with the film to be described later to realize a cell culture sheet. In addition, if the conditions of the fiber diameter and the basis weight of the fibrous web are not satisfied, it may be difficult to realize a surface morphology suitable for cell culture, and it may be difficult to achieve the desired level of cell culture efficiency of the present invention. On the other hand, in order for the surface of the fibrous web to realize a morphology advantageous for cell culture, particularly stem cell culture, the fibrous web preferably has an average fiber diameter of 200 to 1000 nm, a thickness of 2 to 10 μm, and a basis weight of 3 to 7 $g/m^2$. Through this, the cell culture efficiency is improved and the cultured cells can be cultured to have a smaller diameter than the diameter at the time of seeding, which is advantageous for culturing younger and better cells. In particular, if the thickness is less than 2 μm, there is a risk that the cell proliferation rate may be greatly reduced. In addition, if the thickness exceeds 10 μm, it may be difficult to observe the cells under a microscope, so it may not be easy to observe the proliferating cells.

Next, a cell culture coating layer provided on the above-described fibrous web will be described.

The cell culture coating layer is a layer that provides a cell adhesion surface capable of improving settling and proliferation after cells to be cultured are seeded. The cell culture coating layer is formed by including a function protein for cell culture in which a functional peptide is bound to a mussel adhesive protein.

Referring to FIG. 1, the cell culture coating layer includes a coating film connecting the spaces between some of the fibers positioned on the surface of the fibrous web. The coating film is randomly formed here and there on the surface of the fibrous web, and the morphology formed by the fibers positioned on the surface of the fibrous web and the coating film connecting the fibers can create a more favorable environment for cell culture. In addition, as the coating film does not cover all of one surface of the fibrous web, the medium can flow in and out, and through this, the medium can be supplied to the cells seated on the surface of the fibrous web in three dimensions, thereby increasing the cell culture efficiency.

In addition, the cell culture coating layer may include a cover layer formed on at least a portion of the outer surface of some or all of the fibers forming the fibrous web as well as the coating film. In addition, the coating film may be formed to connect the spaces between some fibers of the fibers positioned inside the fibrous web or fibers positioned on the other surface of the fibrous web, as well as the fibers positioned on the surface of the fibrous web.

The cell culture coating layer, which is formed through a fusion protein for cell culture and includes a coating film that connects the spaces between fibers, is excellent in cell culture efficiency. At the same time, even when stored at room temperature for more than several years, storage stability is greatly improved as the decrease in the activity of functional peptides caused by degradation and denaturation of the fusion protein for cell culture forming the cell culture coating layer is prevented or minimized. In addition, the cell culture coating layer does not use a polymer-based adhesive component, for example, an acrylic adhesive component, and introduces a functional peptide to the surface of the cell culture substrate, so there is no cytotoxicity, and the cells can be cultured more biocompatible.

The cell culture coating layer is formed through the fusion protein for cell culture in which a functional peptide is bound to a mussel adhesive protein, and the functional peptide is a material having a function to help cell culture. Specifically, it may be a material that performs the function of promoting any one or more of cell adhesion, cell migration, cell proliferation, and cell differentiation. As the functional peptide, known peptides performing these functions may be used without limitation. Non-limiting examples include adrenomedullin, angiopoietin, bone morphogenetic protein (BMP), brain-derived neurotrophic factor (BDNF), epidermal growth factor (EGF), erythropoietin, fibroblast growth factor, glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), nerve growth factor (NGF), platelet-derived growth factor (PDGF), thrombopoietin (TPO), T-cell growth factor (TCGF), neuropilin, transforming growth factor-alpha (TGF-α), transforming growth factor-beta (TGF-β), tumor necrosis factor-alpha (TNF-α), vascular endothelial growth factor (VEGF), a predetermined amino acid sequence included in any one or more growth factors (GF) selected from the group consisting of IL-1, IL-2, IL-3, IL-4, IL-5, IL-6 and IL-7. Alternatively, it may include a predetermined amino acid sequence included in any one or one extracellular matrices selected from the group consisting of hyaluronic acid, heparin sulfate, chondroitin sulfate, termatin sulfate, keratan sulfate, alginate, fibrin, fibrinogen, collagen, elastin, fibronectin, vitronectin, cadherin and laminin.

For example, the functional peptide may include an RGD sequence in an amino acid sequence. In addition, the functional peptide may be any one or more peptides selected from the group consisting of the amino acid sequence of SEQ ID NO: 15 to SEQ ID NO: 19 or a peptide to which one or more amino acid sequences selected from the group are linked. In addition, the functional peptide may be a vitronectin polypeptide, a collagen polypeptide, a laminin polypeptide, a fibronectic polypeptide, or a variant thereof.

On the other hand, the functional peptide may be, for example, a peptide having a to b amino acid number, even when stored in a state contained in the coating layer at room temperature for a long time, it may be more advantageous to minimize or prevent degradation, denaturation, and the like.

In addition, the functional peptide is bound to the mussel adhesive protein, and specifically, it may be bound to the carboxy terminus, the amino terminus, or both the carboxy terminus and the amino terminus of the mussel adhesive protein. In this case, the bond may be a covalent bond, specifically, an amino bond. On the other hand, the functional peptide and the mussel adhesive protein can be bound through a known method, and for example, can be prepared through a recombinant protein production method using *E. coli*. On the other hand, the mussel adhesive protein and the functional peptide may be directly covalently bonded, but the present invention is not limited thereto. It is illustrated that the mussel adhesive protein and functional peptide can be indirectly bound by mediating a predetermined material such as a crosslinking agent.

The reasons for binding the functional peptide to the mussel adhesive protein is that the mussel adhesive protein is advantageous for fixing the functional peptides to the fiber surface of the fibrous web with good adhesion properties, and that there is no toxicity that may be applied to cultured cells compared to the polymer-based adhesive component and there is excellent biocompatibility as described above. In addition, there is an advantage in that the dissociation of the seeded cells can be minimized due to good adhesion properties with the seeded cells after the seeded cells are seated on the cell adhesion surface.

The mussel adhesive protein is an adhesive protein derived from mussels, and a known adhesive protein collectively referred to as a mussel adhesive protein may be used without limitation. Preferably, the mussel adhesive protein may be any one protein selected from the group consisting of the amino acid sequences of SEQ ID NO: 1 to SEQ ID NO: 14 or a protein to which one or more amino acid sequences selected from the group are linked. For example, it may be the mussel adhesive protein represented by SEQ ID NO: 13.

On the other hand, the cell culture substrate according to an embodiment of the present invention may further include a support disposed on the other surface opposite to one surface of the fibrous web. For the support, a member that supplements the mechanical strength of the fibrous web may be used without limitation. For example, the support may be a woven fabric, a knitted fabric, a non-woven fabric or a film. In addition, the material of the support is preferably a material that does not affect cell culture, for example, may be a material such as polycarbonate, polystyrene, polyethylene terephthalate, polyimide. Meanwhile, the support and the fibrous web may be attached to each other through thermal fusion by melting a portion of the support and/or a portion of the fibrous web or through a separate adhesive. In this case, the adhesive may be a silicone adhesive that can minimize the influence on cell culture.

The cell culture substrate provided with the above-described cell culture coating layer according to an embodiment of the present invention may be manufactured by the steps of (1) preparing an active solution containing a carbodiimide-based coupling agent and a reactive agent and the fusion protein for cell culture in which the functional peptide is bound to the mussel adhesive protein, (2) mixing the prepared active solution with the fusion protein for cell culture to prepare a cell culture coating composition, and (3) treating the cell culture coating composition on the surface of the fibrous web to form the cell culture coating layer.

First, as the step (1) according to the present invention, the step of preparing the active solution containing a carbodiimide-based coupling agent and a reactive agent and the fusion protein for cell culture in which the functional peptide is bound to the mussel adhesive protein is performed.

The active solution includes a carbodiimide-based coupling agent and a reactive agent, and may further include a solvent. The active solution is a material that introduces the fusion protein for cell culture to the surface of the fibrous web, and improves the adhesion between the cell culture coating layer and the surface of the cell culture substrate compared to the case where the fusion protein for cell culture is simply treated on the surface of the fibrous web by a conventional method.

For the carbodiimide-based coupling agent, a coupling agent that allows the fusion proteins to bind to each other can be used without limitation. For example, it may be 1-[3-(dimethylamino)propyl]-3-ethylcarboimide hydrochloride (EDC) or N,N'-dicyclohexylcarboimide (DCC).

In addition, the reactive agent is provided to prevent the fusion protein in a coupled state with the carbodiimide-based coupling agent from being hydrated, thereby increasing the efficiency of binding the fusion proteins to each other. For example, it may be N-hydroxysulfosuccinimide (Sulfo-NHS). On the other hand, N-hydroxysuccinimide (NHS), which is conventionally known as a reactive agent, may not be suitable to achieve the desired effect of the present invention.

The active solution may contain the carbodiimide-based coupling agent and the reactive agent in a weight ratio of 1:0.1 to 10. If they are not contained in an appropriate ratio, it is difficult to achieve the desired effect of the present invention, and there is a risk that the cell adhesion in the realized cell culture coating layer is significantly reduced.

In addition, the active solution may further contain sodium acetate to improve reactivity. In this case, the sodium acetate may be contained in an amount of 1 to 100 parts by weight based on 100 parts by weight of the carbodiimide-based coupling agent.

In addition, the active solution may further contain a solvent, and the solvent may be water or an organic solvent, for example water.

The method for preparing the active solution is not particularly limited, but, for example, the final active solution may be prepared by adding sodium acetate solution to the carbodiimide-based coupling agent solution and the reactive agent solution, respectively, and mixing them to prepare two types of solutions, and then, mixing the two types of solutions in an appropriate ratio and then inducing a reaction for 20 to 50 minutes, and then performing the reaction again for 25 to 40 minutes in an incubator at 28 to 35° C.

Next, as the step (2) according to the present invention, the step of preparing a cell culture coating composition is performed by mixing the prepared active solution and the cell culture fusion protein.

In this case, the fusion protein for cell culture and the active solution may be mixed by adjusting the content so that 1 to 100 parts by weight of the carbodiimide-based coupling agent is contained with respect to 100 parts by weight of the fusion protein for cell culture. If the amount of the carbodiimide-based coupling agent is less than 1 part by weight, cell adhesion may not occur or differentiation may occur, and if it exceeds 100 parts by weight, the cells may be detached after attachment, so it may be difficult to stably culture the cells.

In addition, the prepared active solution and the fusion protein for cell culture can be mixed, and then a reaction is induced for more than 0 to 2 hours to prepare the final cell culture coating composition.

Next, as the step (3) according to the present invention, the cell culture coating composition is treated on the surface of the fibrous web to form a cell culture coating layer.

The method of treating the prepared cell culture coating composition on the surface of the fibrous web may be a commonly used coating method. For example, dispensing using a pipette aid or impregnation may be performed. After the cell culture coating composition is treated on the surface, a reaction can be induced in an incubator at 25 to 32° C. for 30 minutes to 2 hours to form the cell culture coating layer.

Thereafter, a washing process may be further performed, and for example, the washing process may be repeated 2 to 5 times in total for 3 to 6 minutes through tertiary distilled water. After the washing process, it can be naturally dried in the air, and through this, the cell culture substrate can be manufactured.

On the other hand, the moisture content of the cell culture coating layer in the finally manufactured cell culture substrate may be less than 5% as it goes through a drying process. This characteristic is an effect expressed by using the fusion protein according to the present invention. In other words, since commercialized materials that help cell culture cannot be stored for a long time after being treated on the fibrous web, they have no choice but to be used within a few days after being treated on the fibrous web. For this reason, it is common not to go through a drying process after coating. On the other hand, the cell culture substrate according to the present invention can be stored for a long time at room temperature for several years, and as a result, the solvent remaining in the cell culture coating layer or the washing water according to the washing process evaporates, so it can show a very small moisture content.

Table 1 below shows the amino acid sequences for the above-described mussel adhesive protein and functional peptide.

TABLE 1

| SEQ ID NO | Amino acid sequence |
|---|---|
| 1 | Ala Lys Pro Ser Tyr Pro Pro Thr Tyr Lys |
| 2 | Ala Lys Pro Ser Tyr Pro Pro Thr Tyr Lys<br>Ala Lys Pro Ser Tyr Pro Pro Thr Tyr Lys |
| 3 | Ala Lys Pro Ser Tyr Pro Pro Thr Tyr Lys<br>Ala Lys Pro Ser Tyr Pro Pro Thr Tyr Lys |

TABLE 1-continued

| SEQ ID NO | Amino acid sequence |
|---|---|
| | Ala Lys Pro Ser Tyr Pro Pro Thr Tyr Lys<br>Ala Lys Pro Ser Tyr Pro Pro Thr Tyr Lys<br>Ala Lys Pro Ser Tyr Pro Pro Thr Tyr Lys<br>Ala Lys Pro Ser Tyr Pro Pro Thr Tyr Lys |
| 4 | Glu Val His Ala Cys Lys Pro Asn Pro Cys<br>Lys Asn Asn Gly Arg Cys Tyr Pro Asp Gly<br>Lys Thr Gly Tyr Lys Cys Lys Cys Val Gly<br>Gly Tyr Ser Gly Pro Thr Cys Ala Cys |
| 5 | Ala Asp Tyr Tyr Gly Pro Lys Tyr Gly Pro<br>Pro Arg Arg Tyr Gly Gly Gly Asn Tyr Asn<br>Arg Tyr Gly Gly Ser Arg Arg Tyr Gly Gly<br>Tyr Lys Gly Trp Asn Asn Gly Trp Lys Arg<br>Gly Arg Trp Gly Arg Lys Tyr Tyr Glu Phe<br>Glu Phe |
| 6 | Ala Asp Tyr Tyr Gly Pro Lys Tyr Gly Pro<br>Pro Arg Arg Tyr Gly Gly Gly Asn Tyr Asn<br>Arg Tyr Gly Arg Arg Tyr Gly Gly Tyr Lys<br>Gly Trp Asn Asn Gly Trp Lys Arg Gly Arg<br>Trp Gly Arg Lys Tyr Tyr |
| 7 | Gly His Val His Arg His Arg Val Leu His<br>Lys His Val His Asn His Arg Val Leu His<br>Lys His Leu His Lys His Gln Val Leu His<br>Gly His Val His Arg His Gln Val Leu His<br>Lys His Val His Asn His Arg Val Leu His<br>Lys His Leu His Lys His Gln Val Leu His |
| 8 | Ser Ser Glu Glu Tyr Lys Gly Gly Tyr Tyr<br>Pro Gly Asn Ala Tyr His Tyr His Ser Gly<br>Gly Ser Tyr His Gly Ser Gly Tyr His Gly<br>Gly Tyr Lys Gly Lys Tyr Tyr Gly Lys Ala<br>Lys Lys Tyr Tyr Tyr Lys Tyr Lys Asn Ser<br>Gly Lys Tyr Lys Tyr Leu Lys Lys Ala Arg<br>Lys Tyr His Arg Lys Gly Tyr Lys Lys Tyr<br>Tyr Gly Gly Ser Ser |
| 9 | Ser Ser Glu Glu Tyr Lys Gly Gly Tyr Tyr<br>Pro Gly Asn Thr Tyr His Tyr His Ser Gly<br>Gly Ser Tyr His Gly Ser Gly Tyr His Gly<br>Gly Tyr Lys Gly Lys Tyr Tyr Gly Lys Ala<br>Lys Lys Tyr Tyr Tyr Lys Tyr Lys Asn Ser<br>Gly Lys Tyr Lys Tyr Leu Lys Lys Ala Arg<br>Lys Tyr His Arg Lys Gly Tyr Lys Lys Tyr<br>Tyr Gly Gly Gly Ser Ser |
| 10 | Tyr Asp Asp Tyr Ser Asp Gly Tyr Tyr Pro<br>Gly Ser Ala Tyr Asn Tyr Pro Ser Gly Ser<br>His Trp His Gly His Gly Tyr Lys Gly Lys<br>Tyr Tyr Gly Lys Gly Lys Lys Tyr Tyr Tyr<br>Lys Phe Lys Arg Thr Gly Lys Tyr Lys Tyr<br>Leu Lys Lys Ala Arg Lys Tyr His Arg Lys<br>Gly Tyr Lys Lys His Tyr Gly Gly Ser Ser<br>Ser |
| 11 | Ser Ser Glu Glu Tyr Lys Gly Gly Tyr Tyr<br>Pro Gly Asn Thr Tyr His Tyr His Ser Gly<br>Gly Ser Tyr His Gly Ser Gly Tyr His Gly<br>Gly Tyr Lys Gly Lys Tyr Tyr Gly Lys Ala<br>Lys Lys Tyr Tyr Tyr Lys Tyr Lys Asn Ser<br>Gly Lys Tyr Lys Tyr Leu Lys Lys Ala Arg<br>Lys Tyr His Arg Lys Gly Tyr Lys Lys Tyr<br>Tyr Gly Gly Gly Ser Ser |
| 12 | Gly Gly Gly Asn Tyr Arg Gly Tyr Cys Ser<br>Asn Lys Gly Cys Arg Ser Gly Tyr Ile Phe<br>Tyr Asp Asn Arg Gly Phe Cys Lys Tyr Gly<br>Ser Ser Ser Tyr Lys Tyr Asp Cys Gly Asn<br>Tyr Ala Gly Cys Cys Leu Pro Arg Asn Pro<br>Tyr Gly Arg Val Lys Tyr Tyr Cys Thr Lys<br>Lys Tyr Ser Cys Pro Asp Asp Phe Tyr Tyr<br>Tyr Asn Asn Lys Gly Tyr Tyr Tyr Tyr Asn<br>Asp Lys Asp Tyr Phe Asn Cys Gly Ser Tyr<br>Asn Gly Cys Cys Leu Arg Ser Gly Tyr |

TABLE 1-continued

| SEQ ID NO | Amino acid sequence |
|---|---|
| 13 | Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Ala Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 14 | Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 15 | Lys Gly Gly Pro Gln Val Thr Arg Gly Asp Val Phe Thr Met Pro |
| 16 | Gly Ala Cys Arg Gly Asp Cys Leu Gly Ala |
| 17 | Lys Gly Gly Pro Gln Cys Val Thr Arg Gly Asp Val Phe Cys Thr Pro |
| 18 | Arg Gly Asp |
| 19 | Pro His Ser Arg Asn Ser Gly Ser Gly Ser Gly Ser Gly Ser Gly Arg Gly Asp Ser Pro |

EXAMPLES

The present invention will be described in more detail through the following examples, but the following examples are not intended to limit the scope of the present invention, which should be construed to aid understanding of the present invention.

Example 1

A fibrous web formed of sterilized PVDF fibers having an average diameter of 260 nm, and having a basis weight of 4.5 g/m$^2$ and a thickness of 5 μm was prepared. Thereafter, the cell culture coating composition prepared in the following Preparation Example was dispensed on the surface of the fibrous web using a pipette aid, and then reacted for one hour in an incubator at 30° C. to form a cell culture coating layer on the surface of the fibrous web. Thereafter, after washing three times for 5 minutes each using tertiary distilled water, the cell culture substrate was prepared by drying in the air with the plate lid open in a clean bench.

Preparation Example—Preparation of Cell Culture Coating Composition

The fusion protein for cell culture was prepared by binding the amino terminus of the functional peptide of SEQ ID NO: 19 to the carboxy terminus of the mussel adhesive protein of SEQ ID NO: 13. In this case, the fusion protein was prepared by a recombinant protein production method using *E. coli.*

Meanwhile, NaOAc, $NaHCO_3$, and 2-(N-morpholino) ethanesulfonic acid solutions dissolved in tertiary distilled water were first prepared to prepare the active solution, and then added in microtubes in which EDC and Sulfo-NHS reagents were respectively dispensed to prepare the EDC solution and Sulfo-NHS.

To prepare the cell culture coating composition, after the EDC solution was put into a conical tube, a Sulfo-NHS solution was added, and the fusion protein for cell culture was added to the prepared active solution while stirring, followed by stirring to prepare the cell culture coating composition. In this case, the cell culture coating composition contained 1 part by weight of EDC with respect to 100 parts by weight of the fusion protein for cell culture, and EDC and Sulfo-NHS were mixed in a weight ratio of 1:2, and the NaOAc contained in the coating composition was contained so as to be 100 parts by weight based on 100 parts by weight of EDC. In this case, the concentration of the fusion protein for cell culture in the cell culture coating composition was 0.05 mg/ml.

Example 2

The cell culture substrate was manufactured in the same manner as in Example 1, except that the fibrous web formed of PVDF fibers having an average diameter of 500 nm, and having a basis weight of 5.8 g/m$^2$ and a thickness of 3 μm was used.

Comparative Example 1

The cell culture substrate was manufactured in the same manner as in Example 1, except that the fibrous web not coated with the cell culture coating composition was used as the cell culture substrate.

Comparative Example 2

The cell culture substrate was manufactured in the same manner as in Example 2, except that the fibrous web not coated with the cell culture coating composition was used as the cell culture substrate.

Experimental Example 1

Figure 2:
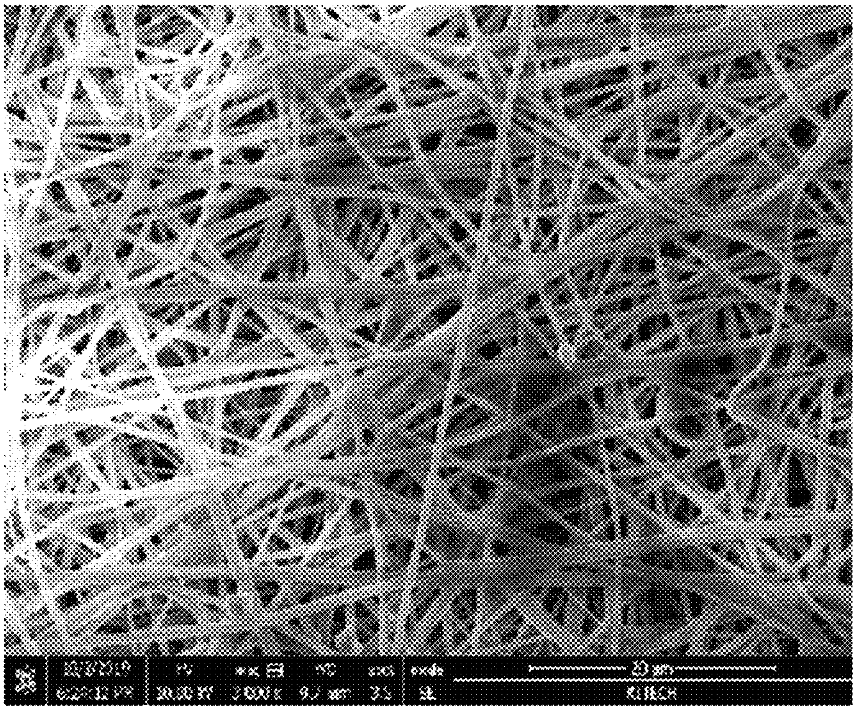
Figure 3:
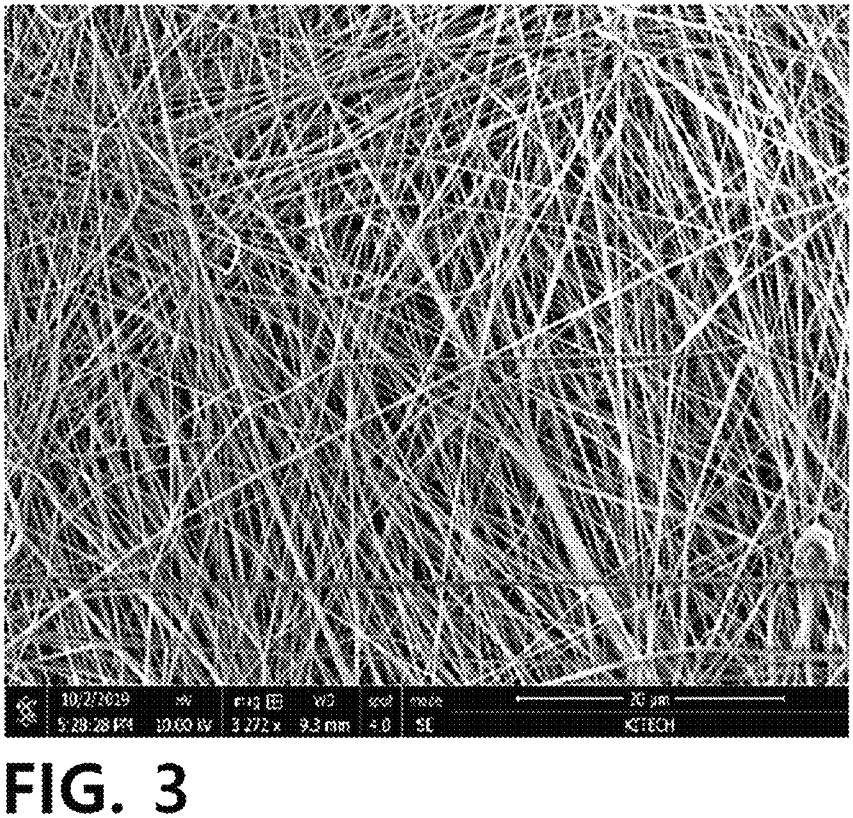
FIGS. 3 and 4 show a SEM photograph of a surface of a cell culture substrate and a photograph of result of cell culture according to a comparative example of the present invention.
Figure 4:
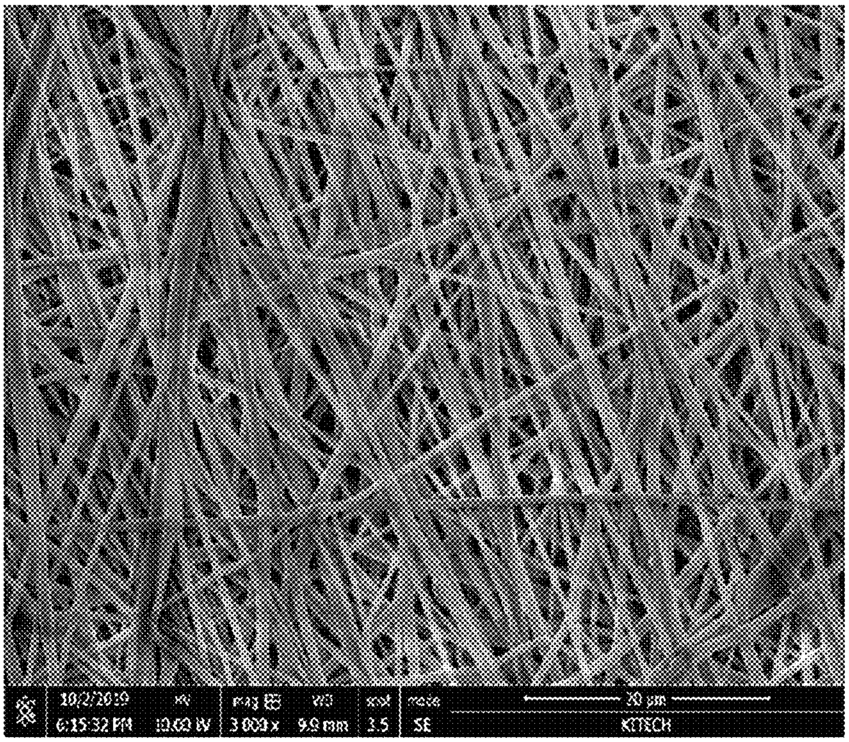

The SEM photographs of the surfaces of the cell culture substrates according to Examples 1 and 2 and Comparative Examples 1 and 2 were taken and shown in FIGS. 1 to 3.

As a result of photographing, it can be observed that in Examples 1 and 2, the cell culture coating layer included the coating film connecting some of the fibers positioned on the surface.

Comparative Examples 3 and 4

A cell culture substrate was manufactured by coating Matrigel and Vitronectin-XF™, which are commercially available as a cell culture coating composition, on the cell culture substrate according to Comparative Example, according to the coating composition manufacturer's protocol.

Experimental Example 2

After dispensing the same amount of induced pluripotent stem cells to the cell culture substrates according to Example 1, Comparative Examples 3 and 4, the cells were cultured in stem cell culture medium (StemMACS™) conditions, and then, the expressions of DAPI, NANOG, SOX2, and Merge markers were observed. The results are shown in FIG. 5 (Example 1), FIG. 6 (Comparative Example 3), and FIG. 7 (Comparative Example 4).

Figure 5:
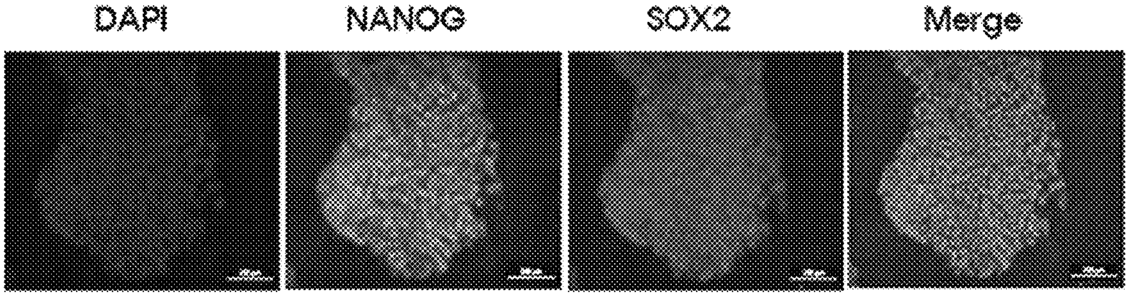
FIGS. 5 to 7 show photographs of expression level of markers of two types (Nanog, Sox2) after culturing induced pluripotent stem cells in cell culture substrates according to an example and a comparative example of the present invention.
Figure 6:
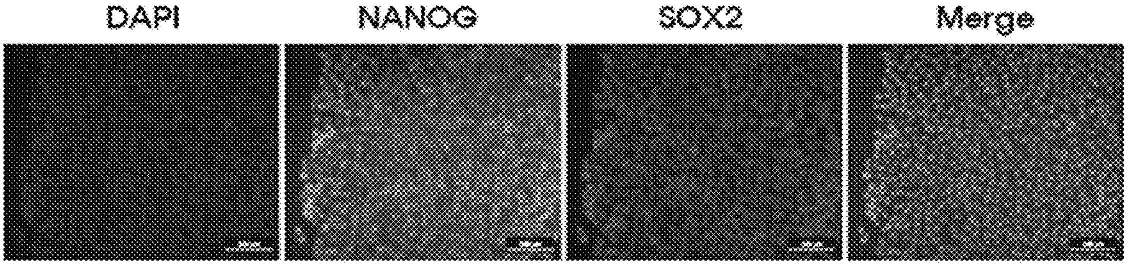
Figure 7:
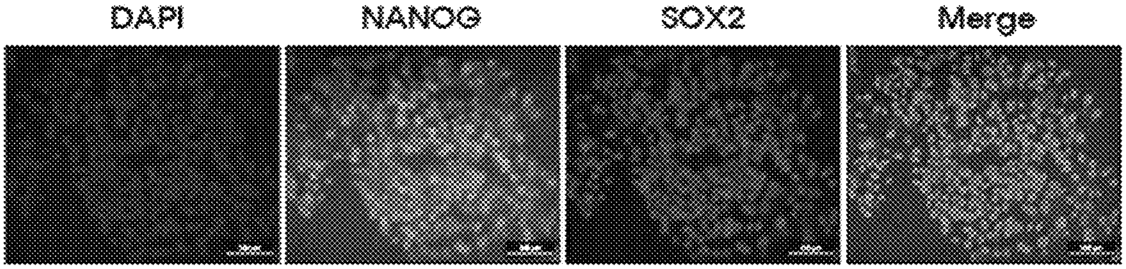

As can be seen from FIGS. 5 to 7, the cell culture substrate according to Example 1 has similar cell culture ability compared to commercially available Matrigel and Vitronectin-XF™, and it can be seen that undifferentiated markers such as NANOG and SOX2 are well expressed.

Experimental Example 3

After dispensing the same amount of induced pluripotent stem cells to the cell culture substrates according to Example 1 and Comparative Example 3, the cells were cultured in stem cell culture medium (StemMACS™) conditions. Then, the morphologies of passage 1 (P1) and passage 13 (P13) of the cultured cells were stained by a cell staining method, and the results of cell culture were shown in FIG. 8. In addition, the growth rate over time was confirmed through absorbance analysis, and the results were shown in FIG. 9. In addition, the expressions of an OCT4 marker for passage 3 (P3) and passage 9 (P9) were confirmed and evaluated by immunocytochemistry, respectively, were shown in FIG. 10. In addition, after culturing the induced pluripotent stem cells in the stem cell culture medium (StemMACS™) conditions for 5 days, the expression level for the Oct4 marker was evaluated, and the results were shown in FIGS. 11 (Example 1) and 12 (Comparative Example 3).

Figure 8:
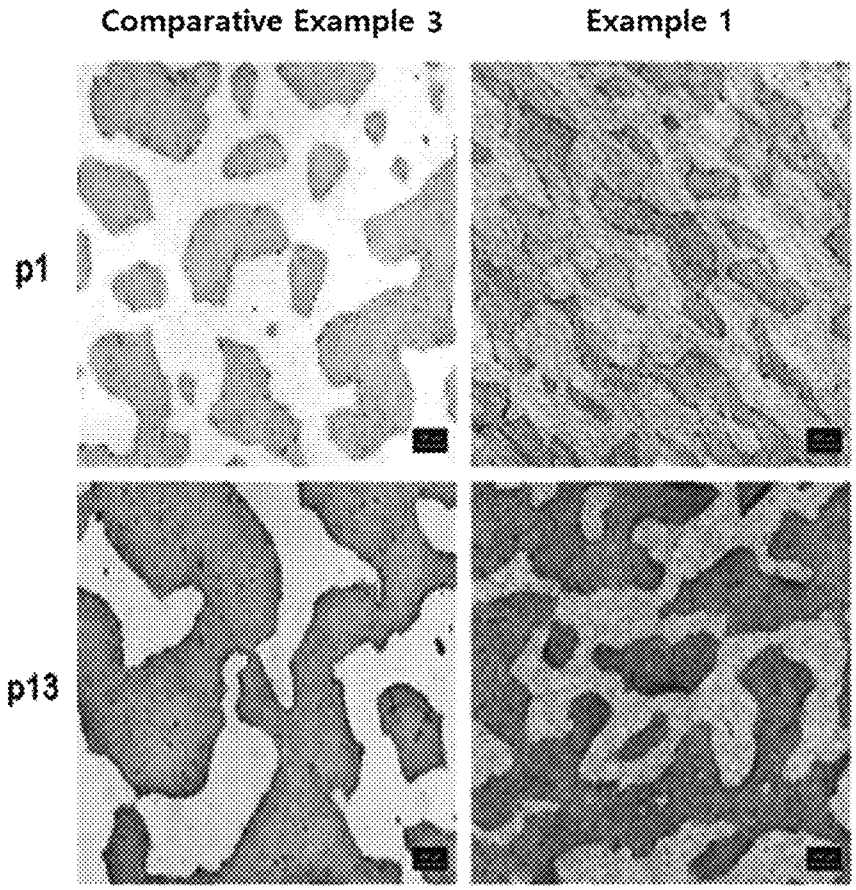
FIG. 8 shows photographs of the culture results obtained by staining the cultured cells at passage 1 and passage 13 by a cell staining method, after induced pluripotent stem cells are subcultured 13 times under the same conditions in cell culture substrates according to an example and a comparative example of the present invention.

As can be seen in FIG. 8, when compared with Comparative Example 3, which is the cell culture substrate using a commercially available cell culture coating composition, the cell culture substrate according to Example 1 is, as can be seen from passages 1 and 13, even when cultured for a long time, it can be seen that there is no difference in morphology.

Figure 9:
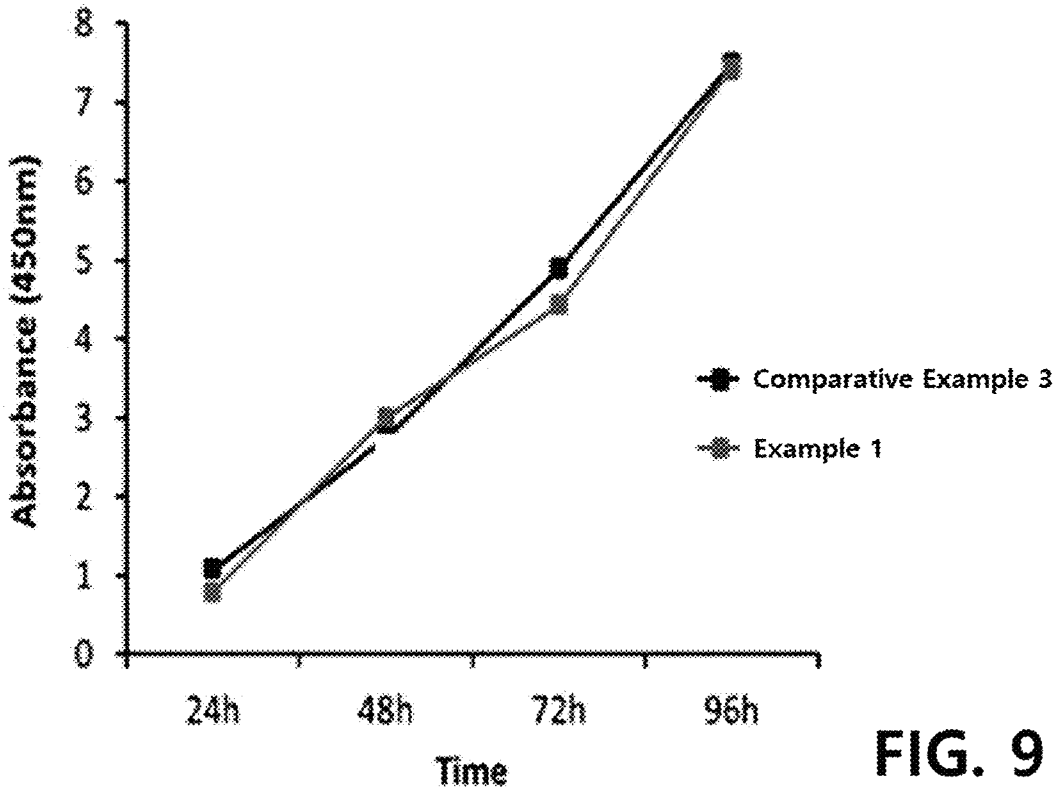
FIG. 9 shows a graph of cell growth measurement through absorbance of the number of cultured cells for each hour after culturing induced pluripotent stem cells in cell culture substrates according to an example and a comparative example of the present invention.

In addition, as can be seen from FIG. 9, the doubling time for Example 1 was 29.2 hours and the doubling time for Comparative Example 3 was 29.0 hours, it can be seen that similar performance is expressed in cell culture efficiency.

Figure 10:
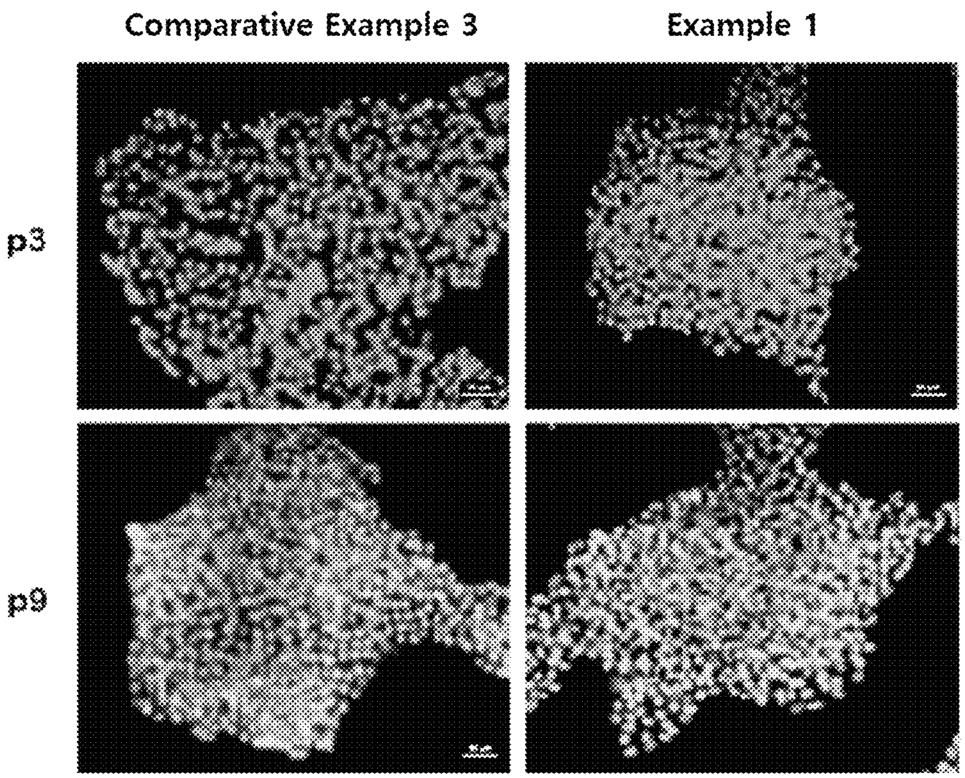
FIG. 10 shows photographs of cultured cells expressing an Oct4 marker at passages 3 and 9 after subculture of induced pluripotent stem cells in cell culture substrates according to an example and a comparative example of the present invention.

In addition, as can be seen from FIG. 10, the cell culture substrate according to Example 1 showed higher expression of the Oct4 in passages 3 and 9 even when cultured for a long time and showed similar cell culture performance, compared to Comparative Example 3, which is the cell culture substrate using a commercially available cell culture coating composition.

Figure 11:
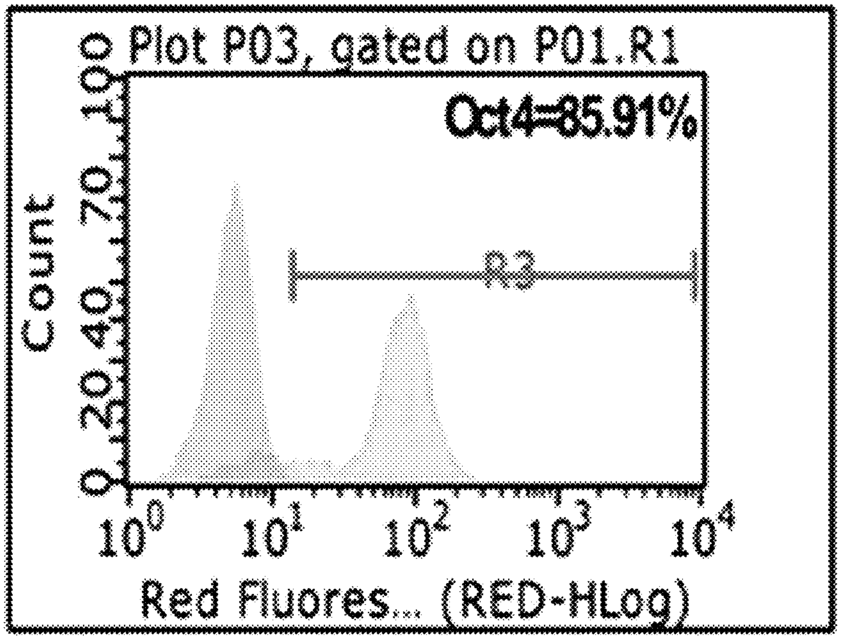
FIGS. 11 and 12 show graphs of evaluation of expression level of cells expressing an Oct4 marker using a flow cytometer after culturing induced pluripotent stem cells in cell culture substrates according to an example and a comparative example of the present invention.
Figure 12:
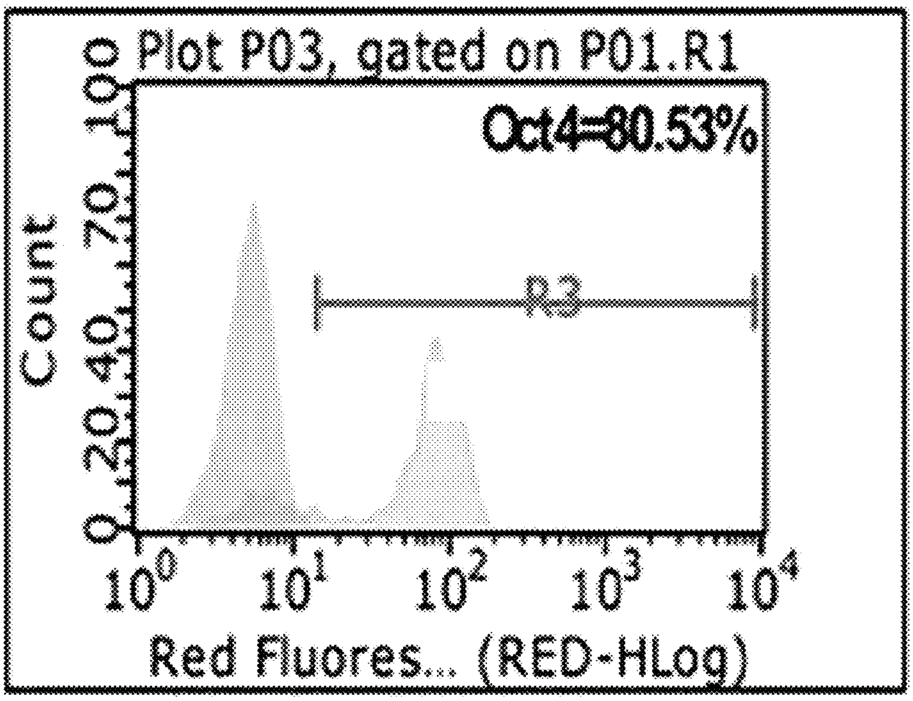

In addition, as can be seen from FIGS. 11 and 12, it can be seen that, when cultured through the cell culture substrate according to Example 1, the expression of Oct4, a cell-specific marker, is higher.

Comparative Example 5

The cell culture substrate was manufactured in the same manner as in Comparative Example 3, except that the fibrous web was changed to the fibrous web of Comparative Example 4.

Comparative Example 6

The cell culture substrate was manufactured in the same manner as in Comparative Example 4, except that the fibrous web was changed to the fibrous web of Comparative Example 4.

Experimental Example 4

The cell culture substrates according to Example 1, Example 2, Comparative Examples 3 to 6 were subjected to an accelerated aging test according to the guidelines for setting of shelf-life evaluation of medical device and stability evaluation in the following manner, and then induced pluripotent stem cells were cultured and the storage stability was evaluated.

Specifically, in order to reproduce the real-time aging of the cell culture substrate within a shortened time, the cell culture substrate was stored at an elevated temperature (60° C.) for 0 month, 1 month, 2 months, and 3 months, and the aging period of each cell culture substrate was set to be 0 year, 1 year, 2 years, and 3 years.

Figure 13:
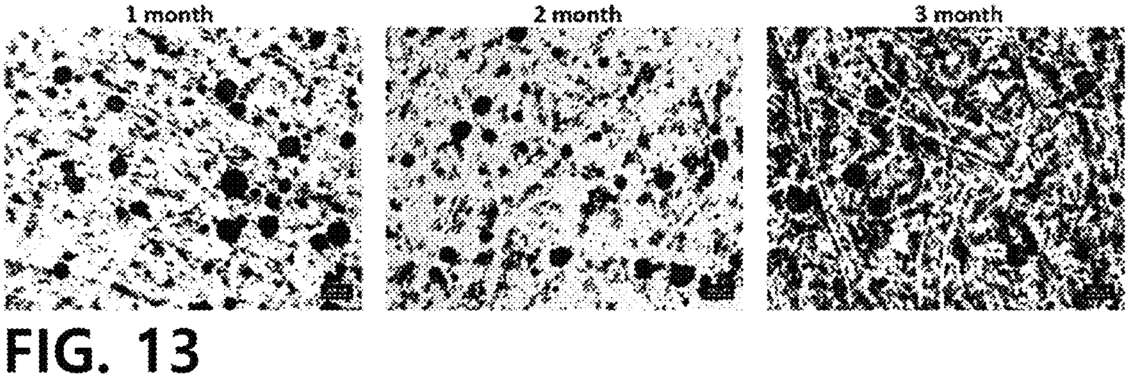
FIGS. 13 to 15 show photographs of culturing induced pluripotent stem cells after performing an accelerated experiment for 1 to 3 months, respectively, for cell culture substrates according to an example and a comparative example of the present invention.
Figure 14:
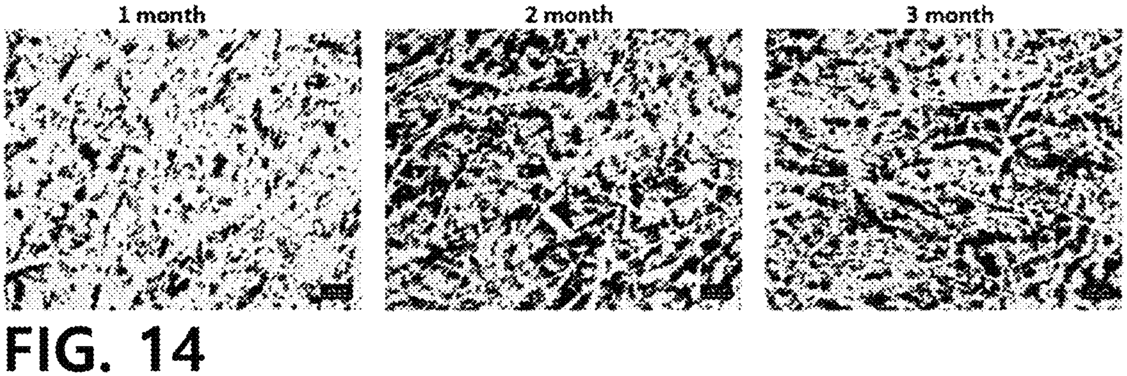
Figure 15:
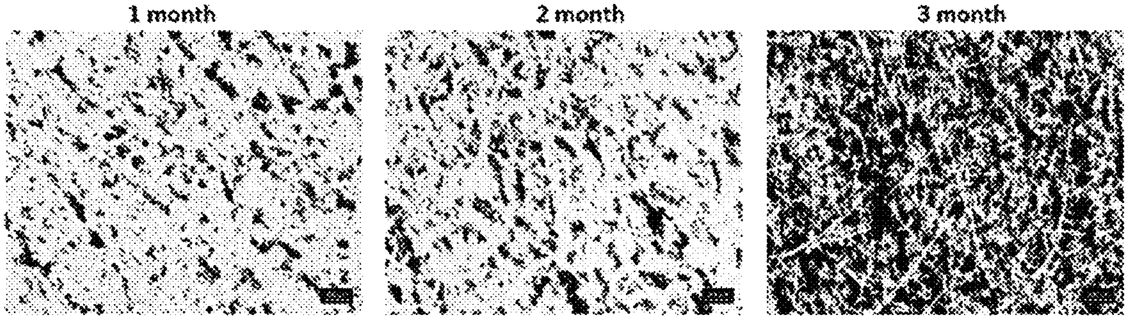
Figure 16:
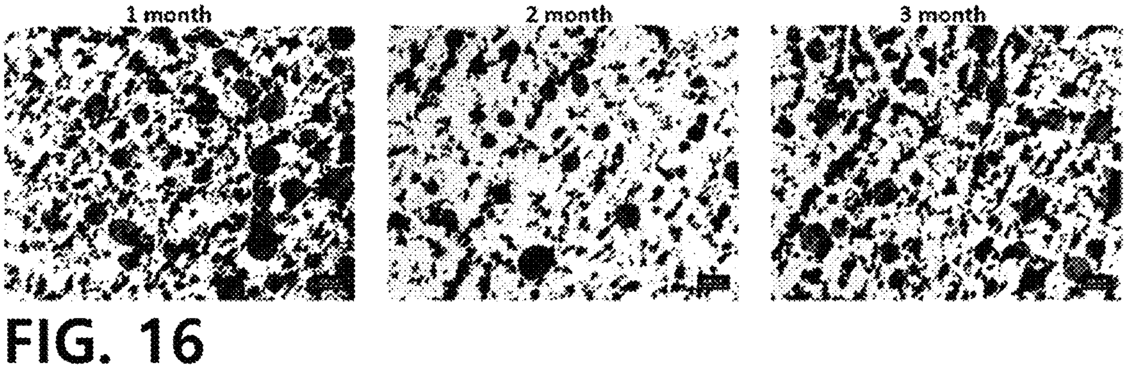
FIGS. 16 to 18 show photographs of culturing induced pluripotent stem cells after performing an accelerated experiment for 1 to 3 months, respectively, on cell culture substrates according to an example and a comparative example of the present invention.
Figure 17:
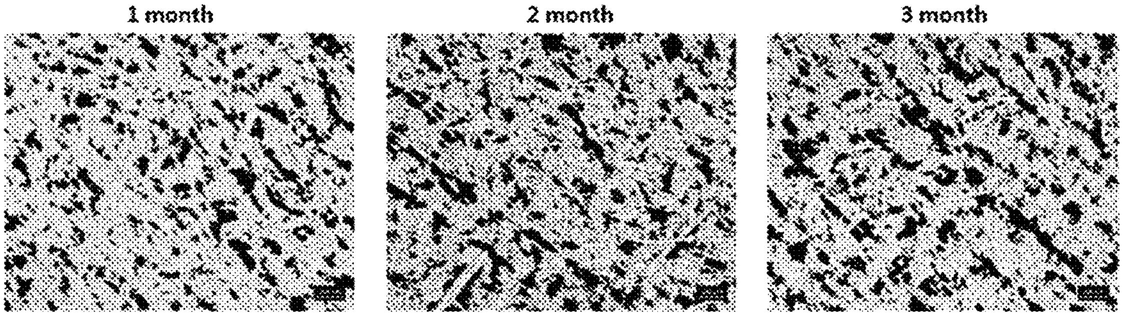
Figure 18:
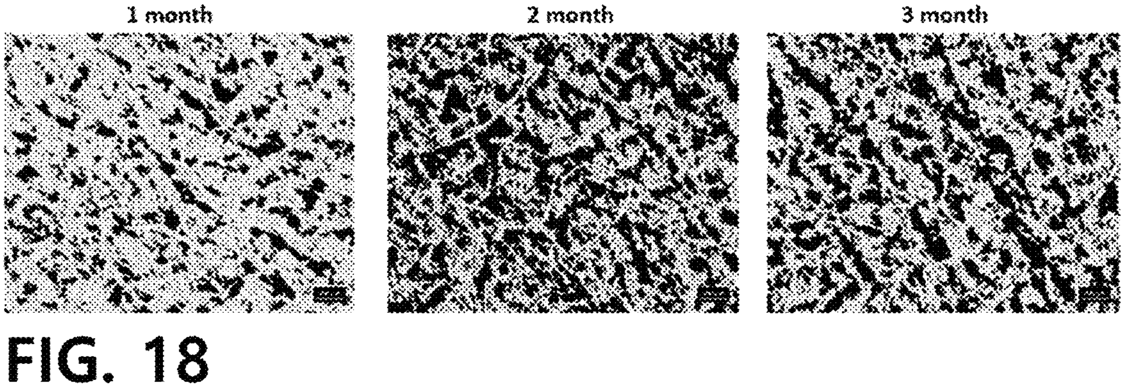

After dispensing the same amount of induced pluripotent stem cells in each of the three cell culture substrates prepared for each Example and Comparative Example, the stem cells were cultured for 5 days using a stem cell culture medium (StemMACS™). The results of cell culture were confirmed with the staining of a cell staining method, and photographed under an optical microscope. The resulting photographs of cell culture are shown in FIGS. 13 (Example 1), 14 (Comparative Example 3), 15 (Comparative Example 4), 16 (Example 2), 17 (Comparative Example 5), 18 (Comparative Example 6).

As can be seen from FIGS. 13 to 18, even when the cell culture substrates according to Examples 1 and 2 had accelerated aging so that the aging period is 1, 2, or 3 years, the cells were cultured in all cell culture substrates and the cell culture ability was high. However, in the cell culture substrates of Comparative Examples 3 to 6, the cells were not cultured in the specimens in which the aging period was accelerated to 1 to 3 years. Through this, it can be seen that the storage stability and cell culture ability of the cell culture substrate according to Example 1 are excellent.

Although one embodiment of the present invention has been described above, the spirit of the present invention is not limited to the embodiments presented herein. Those skilled in the art who understand the spirit of the present invention will be able to easily suggest other embodiments by including, changing, deleting, or adding components within the scope of the same spirit, but this is also said to be within the scope of the present invention.

The invention claimed is:

1. A cell culture substrate, comprising:

a fibrous web in which fibers are integrated; and a cell culture coating layer comprising a coating film connecting at least some of the fibers positioned on one surface of the fibrous web and blocking some pores formed on the surface, wherein the cell culture coating layer is formed with a fusion protein for cell culture in which a functional peptide that promotes any one or more of adhesion, migration, proliferation and differentiation of a cell is bound to a mussel adhesive protein.

2. The cell culture substrate according to claim 1, wherein the fibrous web includes any one or more components selected from the group consisting of polystyrene (PS), polyester, polyethersulfone (PES), polyvinylidene fluoride (PVDF), polydimethylsiloxane (PDMS), polyamide, polyimide, polyethylene and polypropylene.

3. The cell culture substrate according to claim 1, wherein the mussel adhesive protein is any one protein selected from the group consisting of amino acid sequences of SEQ ID NO: 1 to SEQ ID NO: 14, or a protein to which one or more amino acid sequences selected from the group are linked.

4. The cell culture substrate according to claim 1, wherein the functional peptide comprises an RGD sequence.

5. The cell culture substrate according to claim 1, wherein the functional peptide is any one or more peptides selected from the group consisting of amino acid sequences of SEQ ID NO: 15 to SEQ ID NO: 19, or a peptide to which one or more amino acid sequences selected from the group are linked.

6. The cell culture substrate according to claim 1, further comprising a support disposed on the other surface opposite to the one surface of the fibrous web.

7. The cell culture substrate according to claim 1, wherein the fibrous web has an average diameter of 200 to 1000 nm, a thickness of 2 to 20 μm, and a basis weight of 3 to 20 $g/m^2$.

8. A method for manufacturing a cell culture substrate, comprising the steps of:

(1) preparing an active solution containing a carbodiimide-based coupling agent and a reactive agent comprising N-hydroxysulfosuccinimide (Sulfo-NHS), and preparing a fusion protein for cell culture in which a functional peptide that promotes any one or more of adhesion, migration, proliferation, and differentiation of a cell is bound to a mussel adhesive protein;

(2) preparing a cell culture coating composition by mixing the prepared active solution and the prepared fusion protein for cell culture; and (3) forming a cell culture coating layer by treating the cell culture coating composition on a surface of a fibrous web.

9. The method for manufacturing a cell culture substrate according to claim 8, wherein the carbodiimide-based coupling agent is 1-ethyl-3-(3-dimethylaminopropyl carbodiimide hydrochloride (EDC) or N,N'-dicyclohexylcarboimide (DCC).

10. The method for manufacturing a cell culture substrate according to claim 8, wherein the carbodiimide-based coupling agent and the reactive agent are contained in the active solution in a weight ratio of 1:0.1 to 10, and in the cell culture coating composition, the carbodiimide-based coupling agent is mixed in an amount of 1:1 to 100 parts by weight with respect to 100 parts by weight of the fusion protein for cell culture.

11. A cell culture coating composition for a porous cell culture substrate which forms a coating layer that blocks at least some pores on a surface of the porous cell culture substrate, the cell culture coating composition comprising a fusion protein for cell culture in which a functional peptide that promotes any one or more of adhesion, migration, proliferation, and differentiation of a cell is bound to a mussel adhesive protein, a carbodiimide-based coupling agent, and a reactive agent comprising N-hydroxysulfosuccinimide (Sulfo-NHS).

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: mussel adhesive protein

<400> SEQUENCE: 1

Ala Lys Pro Ser Tyr Pro Pro Thr Tyr Lys
1               5                   10


<210> SEQ ID NO 2
<211> LENGTH: 20
<212> TYPE: PRT
<213> ORGANISM: Artificial Sequence
<220> FEATURE:
<223> OTHER INFORMATION: mussel adhesive protein

<400> SEQUENCE: 2

Ala Lys Pro Ser Tyr Pro Pro Thr Tyr Lys Ala Lys Pro Ser Tyr Pro
1               5                   10                  15

Pro Thr Tyr Lys
            20


<210> SEQ ID NO 3
<211> LENGTH: 60
<212> TYPE: PRT
<213> ORGANISM: Artificial Sequence
<220> FEATURE:
<223> OTHER INFORMATION: mussel adhesive protein

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60


<210> SEQ ID NO 4
<211> LENGTH: 39
<212> TYPE: PRT
<213> ORGANISM: Artificial Sequence
<220> FEATURE:
<223> OTHER INFORMATION: mussel adhesive protein

<400> SEQUENCE: 4

Glu Val His Ala Cys Lys Pro Asn Pro Cys Lys Asn Asn Gly Arg Cys
1               5                   10                  15

Tyr Pro Asp Gly Lys Thr Gly Tyr Lys Cys Lys Cys Val Gly Gly Tyr
            20                  25                  30

Ser Gly Pro Thr Cys Ala Cys
        35


<210> SEQ ID NO 5
<211> LENGTH: 52
<212> TYPE: PRT
<213> ORGANISM: Artificial Sequence
<220> FEATURE:
<223> OTHER INFORMATION: mussel adhesive protein
```

<400> SEQUENCE: 5

Ala Asp Tyr Tyr Gly Pro Lys Tyr Gly Pro Pro Arg Arg Tyr Gly Gly
1               5                   10                  15

Gly Asn Tyr Asn Arg Tyr Gly Gly Ser Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Glu Phe Glu Phe
    50

<210> SEQ ID NO 6
<211> LENGTH: 46
<212> TYPE: PRT
<213> ORGANISM: Artificial Sequence
<220> FEATURE:
<223> OTHER INFORMATION: mussel adhesive protein

<400> SEQUENCE: 6

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 7
<211> LENGTH: 60
<212> TYPE: PRT
<213> ORGANISM: Artificial Sequence
<220> FEATURE:
<223> OTHER INFORMATION: mussel adhesive protein

<400> SEQUENCE: 7

Gly His Val His Arg His Arg Val Leu His Lys His Val His Asn His
1               5                   10                  15

Arg Val Leu His Lys His Leu His Lys His Gln Val Leu His Gly His
            20                  25                  30

Val His Arg His Gln Val Leu His Lys His Val His Asn His Arg Val
        35                  40                  45

Leu His Lys His Leu His Lys His Gln Val Leu His
    50                  55                  60

<210> SEQ ID NO 8
<211> LENGTH: 75
<212> TYPE: PRT
<213> ORGANISM: Artificial Sequence
<220> FEATURE:
<223> OTHER INFORMATION: mussel adhesive protein

<400> SEQUENCE: 8

Ser Ser Glu Glu Tyr Lys Gly Gly Tyr Tyr Pro Gly Asn Ala Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser 65 70 75

<210> SEQ ID NO 9
<211> LENGTH: 76
<212> TYPE: PRT
<213> ORGANISM: Artificial Sequence
<220> FEATURE:
<223> OTHER INFORMATION: mussel adhesive protein

<400> SEQUENCE: 9

Ser Ser Glu Glu Tyr Lys Gly Gly Tyr Tyr Pro Gly Asn Thr Tyr His
1 5 10 15

Tyr His Ser Gly Gly Ser Tyr His Gly Ser Gly Tyr His Gly Gly Tyr
20 25 30

Lys Gly Lys Tyr Tyr Gly Lys Ala Lys Lys Tyr Tyr Tyr Lys Tyr Lys
35 40 45

Asn Ser Gly Lys Tyr Lys Tyr Leu Lys Lys Ala Arg Lys Tyr His Arg
50 55 60

Lys Gly Tyr Lys Lys Tyr Tyr Gly Gly Gly Ser Ser
65 70 75

<210> SEQ ID NO 10
<211> LENGTH: 71
<212> TYPE: PRT
<213> ORGANISM: Artificial Sequence
<220> FEATURE:
<223> OTHER INFORMATION: mussel adhesive protein

<400> SEQUENCE: 10

Tyr Asp Asp Tyr Ser Asp Gly Tyr Tyr Pro Gly Ser Ala Tyr Asn Tyr
1 5 10 15

Pro Ser Gly Ser His Trp His Gly His Gly Tyr Lys Gly Lys Tyr Tyr
20 25 30

Gly Lys Gly Lys Lys Tyr Tyr Tyr Lys Phe Lys Arg Thr Gly Lys Tyr
35 40 45

Lys Tyr Leu Lys Lys Ala Arg Lys Tyr His Arg Lys Gly Tyr Lys Lys
50 55 60

His Tyr Gly Gly Ser Ser Ser
65 70

<210> SEQ ID NO 11
<211> LENGTH: 76
<212> TYPE: PRT
<213> ORGANISM: Artificial Sequence
<220> FEATURE:
<223> OTHER INFORMATION: mussel adhesive protein

<400> SEQUENCE: 11

Ser Ser Glu Glu Tyr Lys Gly Gly Tyr Tyr Pro Gly Asn Thr Tyr His
1 5 10 15

Tyr His Ser Gly Gly Ser Tyr His Gly Ser Gly Tyr His Gly Gly Tyr
20 25 30

Lys Gly Lys Tyr Tyr Gly Lys Ala Lys Lys Tyr Tyr Tyr Lys Tyr Lys
35 40 45

Asn Ser Gly Lys Tyr Lys Tyr Leu Lys Lys Ala Arg Lys Tyr His Arg
50 55 60

Lys Gly Tyr Lys Lys Tyr Tyr Gly Gly Gly Ser Ser
65 70 75

<210> SEQ ID NO 12

<211> LENGTH: 99
<212> TYPE: PRT
<213> ORGANISM: Artificial Sequence
<220> FEATURE:
<223> OTHER INFORMATION: mussel adhesive protein

<400> SEQUENCE: 12

```
Gly Gly Gly Asn Tyr Arg Gly Tyr Cys Ser Asn Lys Gly Cys Arg Ser
1               5                   10                  15

Gly Tyr Ile Phe Tyr Asp Asn Arg Gly Phe Cys Lys Tyr Gly Ser Ser
            20                  25                  30

Ser Tyr Lys Tyr Asp Cys Gly Asn Tyr Ala Gly Cys Cys Leu Pro Arg
        35                  40                  45

Asn Pro Tyr Gly Arg Val Lys Tyr Tyr Cys Thr Lys Lys Tyr Ser Cys
    50                  55                  60

Pro Asp Asp Phe Tyr Tyr Tyr Asn Asn Lys Gly Tyr Tyr Tyr Tyr Asn
65                  70                  75                  80

Asp Lys Asp Tyr Phe Asn Cys Gly Ser Tyr Asn Gly Cys Cys Leu Arg
                85                  90                  95

Ser Gly Tyr
```

<210> SEQ ID NO 13
<211> LENGTH: 194
<212> TYPE: PRT
<213> ORGANISM: Artificial Sequence
<220> FEATURE:
<223> OTHER INFORMATION: mussel adhesive protein

<400> SEQUENCE: 13

```
Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
    50                  55                  60

Tyr Lys Gly Gly Tyr Tyr Pro Gly Asn Ala Tyr His Tyr His Ser Gly
65                  70                  75                  80

Gly Ser Tyr His Gly Ser Gly Tyr His Gly Gly Tyr Lys Gly Lys Tyr
                85                  90                  95

Tyr Gly Lys Ala Lys Lys Tyr Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
        115                 120                 125

Tyr Tyr Gly Gly Ser Ser Ala Lys Pro Ser Tyr Pro Pro Thr Tyr Lys
    130                 135                 140

Ala Lys Pro Ser Tyr Pro Pro Thr Tyr Lys Ala Lys Pro Ser Tyr Pro
145                 150                 155                 160

Pro Thr Tyr Lys Ala Lys Pro Ser Tyr Pro Pro Thr Tyr Lys Ala Lys
                165                 170                 175

Pro Ser Tyr Pro Pro Thr Tyr Lys Ala Lys Pro Ser Tyr Pro Pro Thr
            180                 185                 190

Tyr Lys
```

<210> SEQ ID NO 14
<211> LENGTH: 196

<212> TYPE: PRT
<213> ORGANISM: Artificial Sequence
<220> FEATURE:
<223> OTHER INFORMATION: mussel adhesive protein

<400> SEQUENCE: 14

Ala Lys Pro Ser Tyr Pro Pro Thr Tyr Lys Ala Lys Pro Ser Tyr Pro
1 5 10 15

Pro Thr Tyr Lys Ala Lys Pro Ser Tyr Pro Pro Thr Tyr Lys Ala Lys
20 25 30

Pro Ser Tyr Pro Pro Thr Tyr Lys Ala Lys Pro Ser Tyr Pro Pro Thr
35 40 45

Tyr Lys Ala Lys Pro Ser Tyr Pro Pro Thr Tyr Lys Ser Ser Glu Glu
50 55 60

Tyr Lys Gly Gly Tyr Tyr Pro Gly Asn Thr Tyr His Tyr His Ser Gly
65 70 75 80

Gly Ser Tyr His Gly Ser Gly Tyr His Gly Gly Tyr Lys Gly Lys Tyr
85 90 95

Tyr Gly Lys Ala Lys Lys Tyr Tyr Tyr Lys Tyr Lys Asn Ser Gly Lys
100 105 110

Tyr Lys Tyr Leu Lys Lys Ala Arg Lys Tyr His Arg Lys Gly Tyr Lys
115 120 125

Lys Tyr Tyr Gly Gly Gly Ser Ser Ala Lys Pro Ser Tyr Pro Pro Thr
130 135 140

Tyr Lys Ala Lys Pro Ser Tyr Pro Pro Thr Tyr Lys Ala Lys Pro Ser
145 150 155 160

Tyr Pro Pro Thr Tyr Lys Ala Lys Pro Ser Tyr Pro Pro Thr Tyr Lys
165 170 175

Ala Lys Pro Ser Tyr Pro Pro Thr Tyr Lys Ala Lys Pro Ser Tyr Pro
180 185 190

Pro Thr Tyr Lys
195

<210> SEQ ID NO 15
<211> LENGTH: 15
<212> TYPE: PRT
<213> ORGANISM: Artificial Sequence
<220> FEATURE:
<223> OTHER INFORMATION: functional peptide

<400> SEQUENCE: 15

Lys Gly Gly Pro Gln Val Thr Arg Gly Asp Val Phe Thr Met Pro
1 5 10 15

<210> SEQ ID NO 16
<211> LENGTH: 10
<212> TYPE: PRT
<213> ORGANISM: Artificial Sequence
<220> FEATURE:
<223> OTHER INFORMATION: functional peptide

<400> SEQUENCE: 16

Gly Ala Cys Arg Gly Asp Cys Leu Gly Ala
1 5 10

<210> SEQ ID NO 17
<211> LENGTH: 16
<212> TYPE: PRT
<213> ORGANISM: Artificial Sequence
<220> FEATURE:
<223> OTHER INFORMATION: functional peptide -continued

```
<400> SEQUENCE: 17

Lys Gly Gly Pro Gln Cys Val Thr Arg Gly Asp Val Phe Cys Thr Pro
1               5                   10                  15


<210> SEQ ID NO 18
<211> LENGTH: 3
<212> TYPE: PRT
<213> ORGANISM: Artificial Sequence
<220> FEATURE:
<223> OTHER INFORMATION: functional peptide

<400> SEQUENCE: 18

Arg Gly Asp
1


<210> SEQ ID NO 19
<211> LENGTH: 20
<212> TYPE: PRT
<213> ORGANISM: Artificial Sequence
<220> FEATURE:
<223> OTHER INFORMATION: functional peptide

<400> SEQUENCE: 19

Pro His Ser Arg Asn Ser Gly Ser Gly Ser Gly Ser Gly Ser Gly Arg
1               5                   10                  15

Gly Asp Ser Pro
            20
```